United States Patent
Noguchi et al.

(10) Patent No.: US 7,228,035 B2
(45) Date of Patent: Jun. 5, 2007

(54) OPTICAL FIBER MACHINING METHOD AND END PROCESSING DEVICE FOR OPTICAL FIBER

(75) Inventors: Hidetoshi Noguchi, Tochigi-ken (JP); Kanji Matsutani, Tochigi-ken (JP); Toshiyuki Takase, Tochigi-ken (JP)

(73) Assignee: Mani, Inc., Tochigi-ken (JP)

( * ) Notice: Subject to any disclaimer, the term of this patent is extended or adjusted under 35 U.S.C. 154(b) by 0 days.

(21) Appl. No.: 11/170,404

(22) Filed: Jun. 29, 2005

(65) Prior Publication Data

US 2006/0018600 A1 Jan. 26, 2006

(51) Int. Cl.
*G02B 6/26* (2006.01)
(52) U.S. Cl. .......................................... 385/43; 385/147
(58) Field of Classification Search .................. 385/43, 385/147; 264/1.24
See application file for complete search history.

(56) References Cited

U.S. PATENT DOCUMENTS 3,715,285 A 2/1973 Tsuchiya et al.
6,051,211 A 4/2000 Hansenne et al.
2003/0022081 A1* 1/2003 Inoue et al. ................. 430/105

FOREIGN PATENT DOCUMENTS

| EP | 1 123 603 A1 | 9/2001 |
|---|---|---|
| GB | 2154 761 A | 9/1985 |
| WO | WO 91/06251 A | 5/1991 |

* cited by examiner

Primary Examiner—Sarah Song
(74) Attorney, Agent, or Firm—Townsend & Banta

(57) ABSTRACT

A method for machining an optical fiber comprises the steps of: connecting a rear end 1b of an optical fiber 1 to a laser oscillator 2 and exposing a clad 12 of a front-end 1a thereof; preparing processing agents 4-6 containing metal powder that can absorb a laser beam emitted from the laser oscillator 2; and soaking the front-end 1a of the optical fiber 1 into or bringing it into contact with the processing agent and, in this condition, emitting the laser beam from the laser oscillator 2 to irradiate the processing agent with it.

8 Claims, 4 Drawing Sheets

(a)

(b)

(c)

OPTICAL FIBER MACHINING METHOD AND END PROCESSING DEVICE FOR OPTICAL FIBER

BACKGROUND OF THE INVENTION

1. Field of the Invention

The present invention relates to a machining method and a machining operation for machining a front-end of a laser-beam guiding optical fiber so that the front-end may taper down and a laser beam irradiation device for enabling irradiating a target position with a laser beam by using this optical fiber.

2. Description of the Related Art

In medical treatment, usually, an affected part of the body is irradiated with a laser beam to evaporate an anatomy for treatment or is cut open. A medical device utilizing such a laser beam is configured so that it can guide a laser beam emitted from a laser oscillator to an affected part of the body and irradiate the affected part with the laser beam through a probe. The probe is made of a material which a laser beam can pass through and has its top portion extremely tapered so that when this front-end is brought close to or into contact with a target affected portion of the body, the affected part can be irradiated with the laser beam.

If a laser beam to be utilized can be guided thorough an optical fiber, the probe is provided to a front-end of the optical fiber. The probe is formed by grinding quartz, sapphire, etc. so that it may comprise a tapered end and a mounting portion for the optical fiber. Further, the probe may come in contact with a body fluid of a patient and so needs to be sterilized indispensably, so that it may be necessary to reserve a lot of such probes.

Such probes made of quartz or sapphire have a problem that they may fluctuate in shape and size and so be destabilized and a cost-related problem because it takes a lot of time to machine them and a lot of such probes needs to be used. To solve these problems, recently a front-end of an optical fiber is tapered to use the optical fiber as a probe.

According to such a method for tapering a front-end of an optical fiber, when performing chemical etching on one end of a probe material in a condition where the end is soaked in an etchant, a fluid level of the etchant with respect to the probe material is moved at a predetermined speed (see, for example, Patent Literature 1). Further, such a method is proposed that a probe may be formed by mechanically grinding a front-end of an optical fiber in such a manner that a core portion may be a cutting edge and soaking this end into an etchant so that it may be sharp (see, for example, Patent Literature 2).

Patent Literature 1: Japanese Patent Application Laid-Open (JP-A) No. 07-218516
Patent Literature 2: JP-A No. 2004-12427

SUMMARY OF THE INVENTION

Since a probe used in medical treatment may come in contact with a body fluid of a patient, preferably it is disposed of if used once. In this case, however, a probe made of quartz or sapphire cannot easily be disposed of because it is expensive.

Therefore, it is preferable to taper a front-end of an optical fiber to use it as a probe. It is particularly preferably to cut off a front-end of an optical fiber each time medical treatment ends so that a cut portion can be tapered.

If a technology of Patent Literature 1 is employed to cut off a front-end of an optical fiber and taper a cut portion, it is necessary to provide such control that a relative position of a liquid level with respect to the optical fiber may be changed in a condition where the front-end of the optical fiber is soaked in an etchant; therefore, a problem occurs that the machining is not easy to accomplish. If a technology of Patent Literature 2 is employed, on the other hand, although it is unnecessary to control the liquid level after the optical fiber is soaked into the etchant, it is necessary to perform a process of mechanically grinding the front-end of the optical fiber before etching, so that a problem occurs that the machining is still not easy to accomplish.

In particular, the technologies of Patent Literatures 1 and 2 both need to perform etching indispensably and a highly corrosive chemical is used as the etchant and its vapor or droplet may affect medical facilities around it, so that these technologies cannot readily be used in medical treatment.

It is an object of the present invention to provide a highly safe machining method for machining a front-end of an optical fiber so that the front-end may taper down without providing any special control and also to provide a laser beam irradiation device that can easily realize this machining method.

To solve the above-described problems, an optical fiber machining method related to the present invention for tapering a front-end of an optical fiber that guides a laser beam emitted from a laser oscillator so as to irradiate a target region with it comprises the steps of: connecting one end of the optical fiber to the laser oscillator leaving a clad on the side of the other end in an exposed condition; preparing a processing agent containing metal powder that can absorb the laser beam emitted from the laser oscillator connected to the optical fiber; and soaking the side of the other end of the optical fiber into or bringing it into contact with the processing agent that contains the metal powder and, in this condition, emitting the laser beam from the laser oscillator.

A laser beam irradiation device related to the present invention comprises: a laser oscillator; an optical fiber for guiding a laser beam emitted from the laser oscillator and irradiating a target region with the laser beam; and a retaining member for containing or retaining a processing agent which is used to machine an end of the optical fiber in such a manner that the end may taper down.

An optical fiber machining method related to the present invention comprises the steps of: preparing a processing agent containing metal powder that can absorb a laser beam emitted from a laser oscillator; soaking an end of an optical fiber whose clad is exposed at this end into or bringing the end into contact with the processing agent; and actuating an laser oscillator to emit the laser beam so that the optical fiber including the clad and a core may be machined so as to taper down. The clad is preferably exposed so that its side face is exposed for certain width from the end.

By decomposing the metal powder contained in the processing agent by thus emitting a laser beam from the optical fiber in a condition where the end of the optical fiber is soaked in or in contact with the processing agent and, along with this decomposition, machining the optical fiber excluding its clad and core so that it may taper down, it is possible to machine the optical fiber by an easy operation without need to control a relative position between the optical fiber and the processing agent.

Therefore, there will be no fluctuations due to an operator unlike the case of mechanical grinding and there is no need to use a highly corrosive chemical as in the case of etching, so that it is possible to machine the optical fiber so that it may taper down, safely and stably in a work environment maintained in a good condition.

Further, the laser beam irradiation device related to the present invention comprises a laser oscillator and an optical fiber connected to this laser oscillator and so can irradiate a target region with a laser beam to carry out an intended operation. It further comprises a container that contains a processing agent, so that by exposing a clad of a front-end of the optical fiber and, as occasion demands, cutting the front-end to keep the front-end cylindrical and, in this condition, soaking it into or bringing it into contact with the processing agent contained in the container and actuating the laser oscillator to emit the laser beam, it is possible to machine the front-end of this optical fiber so that it may taper down.

The processing agent in the present invention indispensably needs to contain metal powder that can absorb a laser beam; however, this metal powder can be used as it is or mixed in a liquid or a fine particle or a porous substance can be impregnated with it. In any case, the processing agent can be used in a condition that it contains no corrosive chemicals. Therefore, there is no problem in terms of safety if the container is arranged in an operating range of the operator of the optical fiber.

Therefore, each time the optical fiber is used, its front-end can be formed so as to taper down easily and safely and it is also possible to irradiate a target region with a laser beam emitted from the front-end thus tapered in machining.

DESCRIPTION OF THE PREFERRED EMBODIMENTS

The following will describe a preferred embodiment of an optical fiber machining method related to the present invention and an embodiment of a laser beam irradiation device on which this machining method can be implemented. The present inventor carried out a lot of experiments to develop a technology for tapering down a front-end of an optical fiber so that this front-end can be utilized as a probe. It results in the present invention.

In these experiments, several kinds of metal powders and non-metal powders were prepared; those metal powders were used directly as fine particles or mixed into water to provide a liquid or a porous substance was impregnated with this liquid to provide an impregnated body; the front-end of the optical fiber was soaked into or brought into contact with these; and in this condition, a laser beam was radiated from a laser oscillator to irradiate the fine particle, the liquid, and the impregnated body with it.

As a result of the experiments, it was found that by soaking the front-end of the optical fiber into or bringing it into contact with a fine particle having metal powder that reacts with a laser beam (that can absorb the laser beam) as a main component, a liquid containing the fine particle, and a body impregnated with the fine particle or the liquid and irradiating them with the laser beam, this front-end can be machined so as to taper down.

Figure 1:
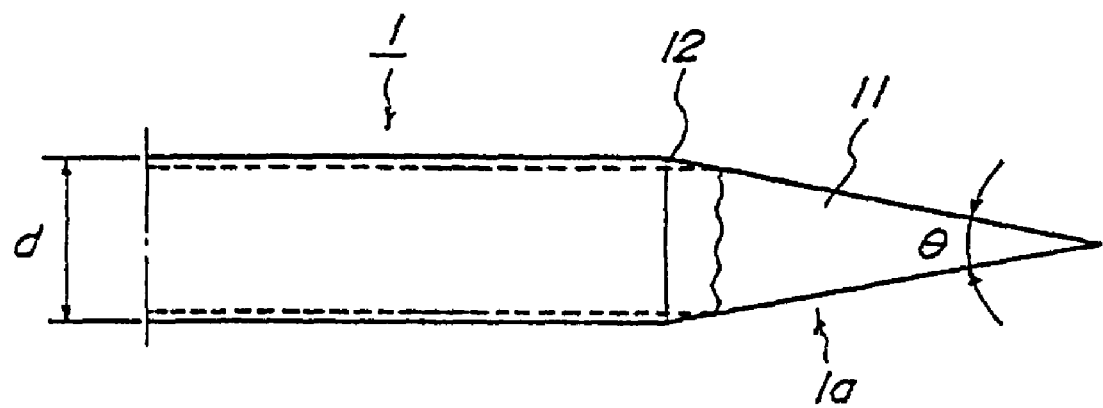
FIG. 1 is an explanatory diagram of a tapered shape of a front-end of an optical fiber.
Figure 2:
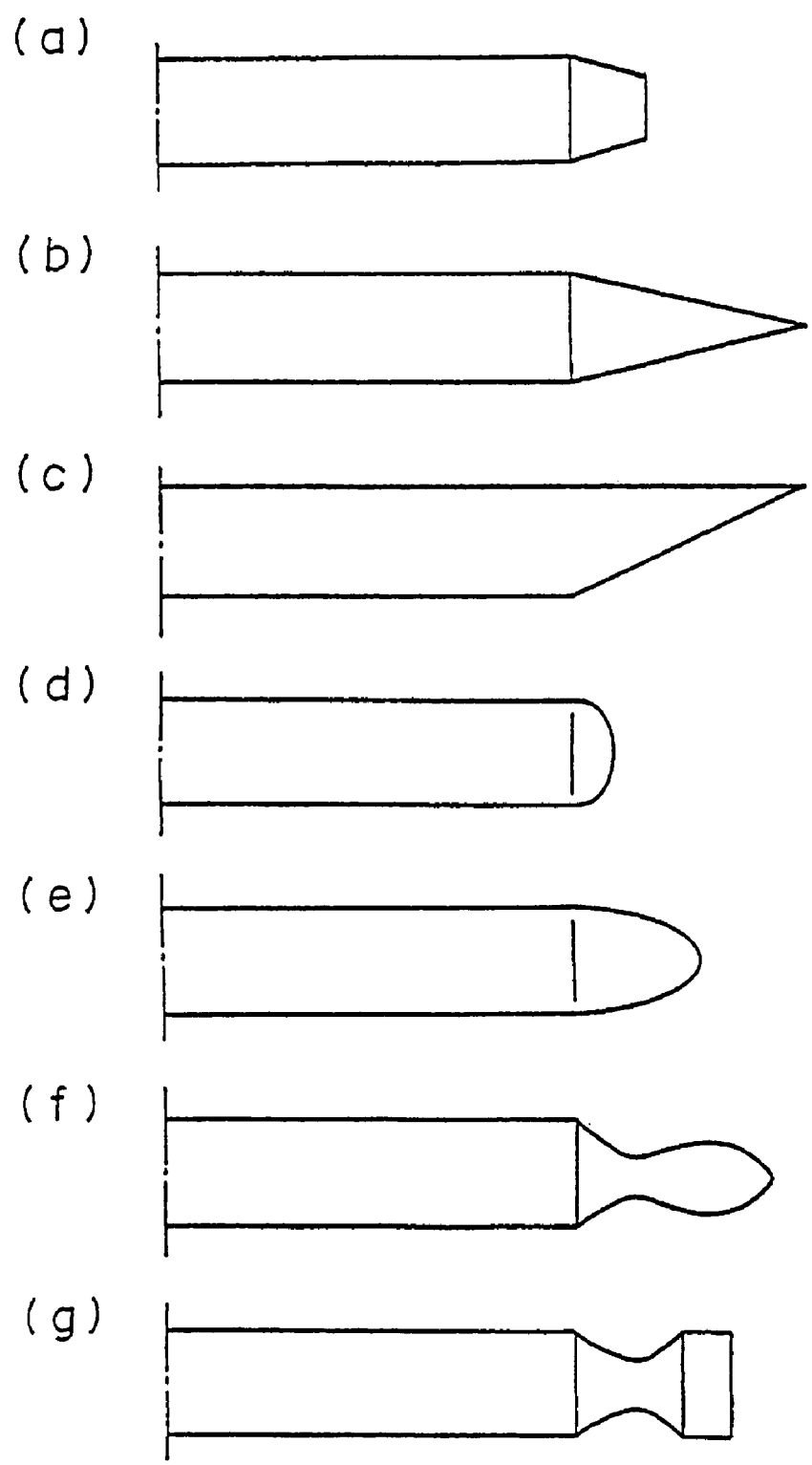
FIG. 2 are explanatory diagrams of examples of the tapered shape.

The following will describe conditions for these experiments as well as their results with reference to FIGS. 1 and 2 qualitatively.

First, a shape into which a front-end 1a of an optical fiber 1 is formed is described. As shown in FIG. 1, the front-end 1a of the optical fiber 1 has a coating (not shown) removed, to expose a core 11 made of quartz glass and a clad 12 made of polymer. This front-end 1a is subjected to machining related to the present invention, to taper down to a point having angle θ.

Next, the experiments are described. As the laser oscillator, an Nd:YAG laser with a wavelength of 1064 nm was used. The optical fibers 1 used each comprises the core 11 made of quartz glass and the clad 12 made of polymer and have diameters d of 200 μm, 300 μm, 400 μm, and 600 μm.

In machining, an energy density (unit: wattage per square millimeters, $W/mm^2$) was set to about 15–320 for the optical fiber's diameter d of 200 μm, about 5–150 for the diameter d of 300 μm, about 5–50 for the diameter d of 400 μm, and about 3–35 for the diameter d of 600 μm, a soaking time for the processing agent was set to 15 seconds, and the number of samples was set to 3 under the same conditions.

As the metal powders, titanium oxide and manganese dioxide were used and as the non-metal powders, calcium chloride and calcium carbonate were used. Those powders were mixed with water to provide processing agents and the front-end 1a of the optical fiber 1 was soaked in these processing agents and these agents were irradiated with a laser beam for 15 seconds to check changes in shape of the front-end 1a. As a result, with titanium oxide, the front-end 1a of the optical fiber 1 was tapered but with the other materials, no changes were observed. That is, it was found that in the case of an Nd:YAG laser with a wavelength of 1064 nm, powder of titanium oxide is effective.

The inventor prepared a fine particle obtained by mixing, by weight, 3% of titanium oxide into silica dioxide powder, a fine particle composed of 100% titanium oxide, liquids obtained by mixing, by weight, 3%, 5%, and 10% of titanium oxide into water, and impregnated bodies obtained by impregnating sponge as a porous body with these liquids and irradiated them with a laser beam for 15 seconds in a condition where the front-end 1a of the optical fiber 1 is soaked in or brought into contact with these fine particle, liquids, and impregnated bodies, to observe changes in shape of this front-end. As a result, it was found that in every case, the front-end can be machined so as to taper down. However, it may be said that the liquid or the impregnated body is preferable to realize stable machining.

Further, the inventor used a micro-grain and a nano-grain as titanium oxide (of rutile structure or anatase structure), mixed this titanium oxide into water to provide a liquid, and irradiated this liquid with a laser beam for 15 seconds in a condition where the front-end 1a of the optical fiber 1 was soaked in this liquid, to check changes in shape of this front-end 1a. As a result, in both cases of these grains of titanium oxide, the front-end could be tapered.

In particular, with smaller granularity of titanium oxide, it was possible to change angle θ in a wider range by changing the energy density in machining. Therefore, it may be said that the granularity should preferably be smaller in order to accommodate a higher degree of freedom for the shape of front-end that changes with an operation purpose.

Further, when the diameter d of the optical fiber was changed, it was found that the front-end could be machined so as to taper down with any value of the diameter. However, under the same conditions of power of the laser oscillator, it was found that the angle θ of the front-end 1a of the thinner optical fiber 1 can be made smaller. It may be considered to be caused by an influence of the energy density.

Similarly, when the energy density was changed with the same diameter d of the optical fiber 1, it was found that the higher the energy density is, the smaller can the angle θ of the front-end 1a be made smaller.

Further, when the irradiation time of the laser beam was made longer than 15 seconds, no conspicuous changes were observed in shape of the front-end 1a of the optical fiber 1. It may be considered to be caused by a fact that after the tapered shape was stabilized once, the whole surface was machined in a condition where roughly the same shape was held.

The following will describe examples of the shape obtained as a result of the experiments, with reference to FIG. 2. FIG. 2A shows a shape obtained when the energy density was somewhat low, which shape is tapered enough to meet the operation purpose. FIG. 2B shows a roughly conical shape and FIG. 2C shows a shape whose end is tapered to one side. FIG. 2D shows a shape whose end is mirror shaped, proving to be one of tapered shapes enough to meet the operation purpose. FIG. 2E shows a shape which is tapered enough to meet the operation purpose, although not acutely tapered. FIGS. 2F and 2G show shapes which are tapered enough to meet the operation purpose, although they have a constriction in the way.

The result of the experiments found that the optical fiber machining method of the present invention can taper a front-end of an optical fiber easily and safely by emitting a laser beam from this optical fiber in a condition where this front-end potion whose clad is exposed is soaked in or brought into contact with a processing agent containing metal powder that can absorb the laser beam.

Further, a laser beam irradiation device of the present invention implements this machining method in a preferable manner and can bring the other end of the optical fiber whose one end is connected to the laser oscillator to a target region and irradiate it with a laser beam through the other end to carry out an intended operation (for example, treatment of an affected part) and also can soak the end of the optical fiber into or bring it into contact with a processing agent contained in a container and emit a laser beam to gradually machine the front-end so that it may taper down.

When a target operation is over with laser beam irradiation of the target region or each time this operation ends, this laser beam irradiation device can machine the end of the optical fiber into a tapered shape so that it can be used as a probe. Therefore, the end of the optical fiber can be machined into a tapered shape easily, thereby realizing an operation with the optical fiber that has a good tapered shape always.

Further, when the laser beam irradiation device of the present invention is used in medical treatment, it is possible to carry out intended treatment by using a new tapered end for a new patent, thereby realizing a highly safe laser beam irradiation device.

The following will describe examples of a laser oscillator, an optical fiber, and a processing agent containing metal powder that are used in the optical fiber machining method or the laser beam irradiation device related to the present invention.

The optical fiber, whose one end is directly or indirectly connected to an output of the laser oscillator, has a function to guide a laser beam emitted from this laser oscillator to a target region. Therefore, a material of the optical fiber is not limited in particular; materials used commonly such as quartz glass or polymer can be used. The diameter of the optical fiber is not limited either; the diameter of the optical fiber may be in a range of 100–600 μm or even larger than this range.

The type and the power of the laser oscillator are not limited in particular either; it is possible to select any types and any powers that are necessary to carry out a target operation of the laser beam irradiation device. In particular, the present invention can be applied to a laser oscillator that can guide an emitted laser beam through an optical fiber. For example, an Nd:YAG laser or a semiconductor laser is available as a laser oscillator for medical treatment; the present invention could well be applied to both of them.

Metal powder that can absorb a laser beam emitted from a laser oscillator (hereinafter referred to as "metal powder" simply) need not be powder of pure metal molecules but may be powder that contains metal oxide. Since metal powder indispensably needs to be able to absorb a laser beam, its material is determined in relation to a wavelength of a laser beam emitted from the laser oscillator. Therefore, the present invention will not restrict the material of the laser oscillator, so that preferably the material may be selected in relation to the laser beam wavelength. As such a metal powder, titanium oxide powder, iron oxide powder, aluminum powder, etc. are available.

The processing agent contains metal powder and is not restricted in terms of a condition in which the metal powder is to be contained. That is, the processing agent may contain a fine particle comprised of the metal powder as it is (100% metal powder), a fine particle obtained by mixing the metal powder into any other powder, or a liquid into which any of these two fine particles is mixed, or even a porous substance impregnated with any of these fine particles and liquid.

That is, the processing agent can be made as a fine particle containing metal powder as its main component, a liquid containing this fine particle, and a body impregnated with this fine particle or liquid, so that the processing agents having these respective natures can be used well by containing them in separate containers.

If the processing agent is made as a fine particle containing metal powder as its main component, a material of the powder that provides a substrate for mixture of the metal powder is not limited in particular, so that the material only needs to be such that the powder may stay as a fine particle even when mixed with the metal powder. The experiments by the present inventor came up with favorable results with the cases of a combination of silica dioxide and manganese dioxide and a combination of calcium chloride and calcium carbonate.

A mixture rate of metal powder in a fine particle containing the metal powder as its main component is not limited in particular and it is possible to set the mixture rate, by weight, to a range of about 3% through 100%. Therefore, a fine particle containing metal powder as its main component or just a fine particle as expressed so is hereinafter to include such as containing 100% powder metal. It is to be noted that the experiments by the present invention proved that the mixture rate has an influence on machining time.

The granularity of metal powder contained in the above-described fine particle is not limited in particular, so that a nano-grain (which has a grain diameter of about 10–100 nm, for example) or a micro-grain (which has a grain diameter of about 0.1–0.5 μm, for example) can be utilized. However, it is proved that even a grain with a diameter outside this range can be machined.

A liquid into which metal powder or a fine particle is contained is not limited in particular, so that any of waters such as clean water, distilled water, and physiological salt solution and oils such as spindle oil and kerosene can be used well. Such a liquid is harmless even in touch with a person around it and so can be held with a high degree of safety. The experiments by the present inventor proved that the liquid can preferably transmit a laser beam without absorbing it.

If clean water is used as the liquid in particular, preferably it is easily available and inexpensive. If a fine particle is contained in the liquid, on the other hand, preferably the mixed fine particle is held to be floating in the liquid. If the mixed fine particle is deposited, good machining is difficult to perform, so that each time machining is carried out, the liquid needs to be stirred. Therefore, preferably an apparent specific gravity of the fine particle is small.

A mixture rate of a fine particle with respect to a liquid is not limited in particular but only needs to be such that fluidity of the liquid can be maintained or that its high viscosity can be exerted.

A substrate to be impregnated with a fine particle or a liquid is not limited in particular but preferably it is porous and flexible enough to be held as impregnated with these. However, its pore size or hardness is not limited. As such a substrate, synthetic resin foam is available; for example, urethane foam can be used.

EXAMPLE 1

Figure 3:
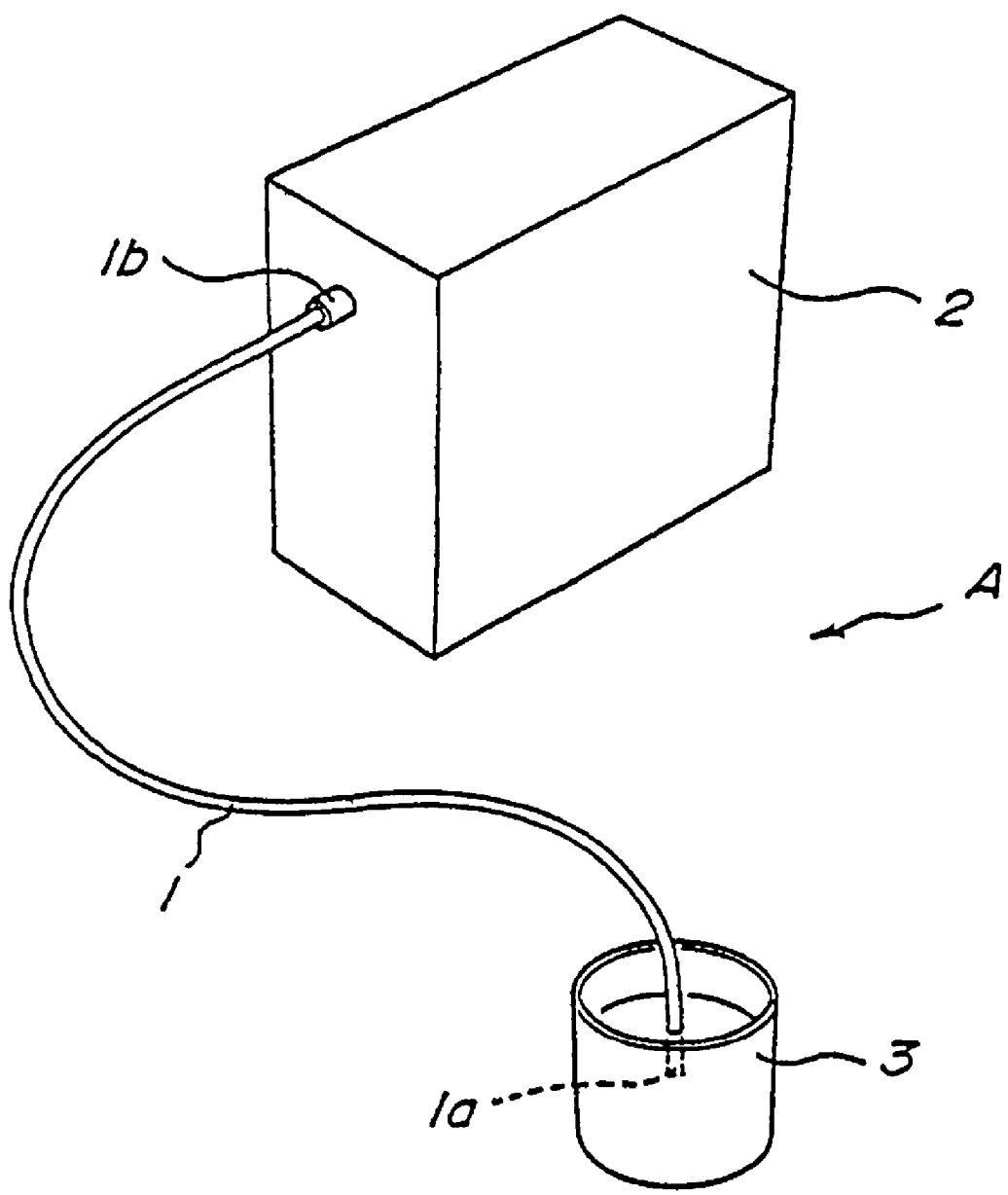
FIG. 3 is an explanatory schematic diagram of a configuration of a laser beam irradiation device.
Figure 4:
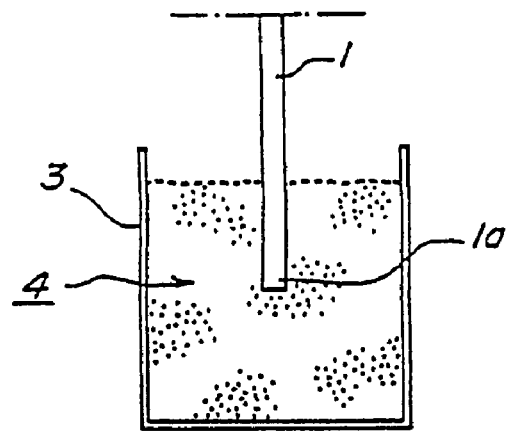
FIG. 4 are explanatory diagrams of conditions in which an end of the optical fiber is soaked into or brought into contact with a processing agent.
Figure 4:
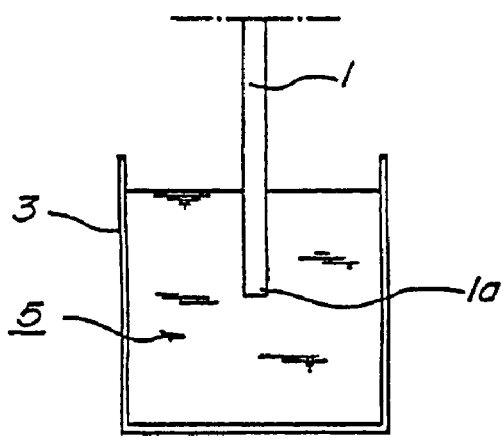
Figure 4:
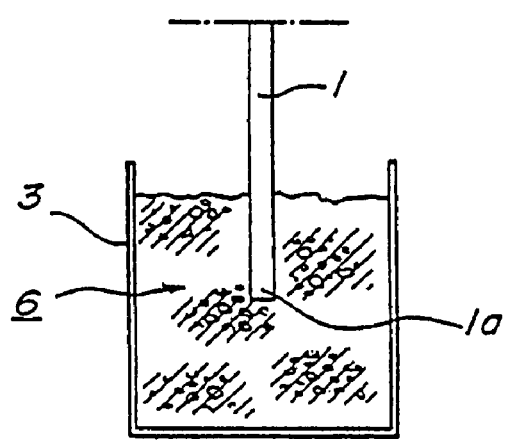

The following will describe an example of a laser beam irradiation device related to the present invention. FIG. 3 is an explanatory schematic diagram of a configuration of the laser beam irradiation device. FIG. 4 are explanatory diagrams of conditions in which an end of the optical fiber is soaked into or brought into contact with a processing agent.

A laser beam irradiation device A shown in the figure comprises a laser oscillator 2 and an optical fiber 1 that is configured so that its one end (rear end) 1b may be connected to the laser oscillator 2 and the other end thereof (front-end) 1a may be tapered so as to be able to function as a probe; therefore, when, for example, a physician brings the front-end 1a into contact with or near a target affected part of a patient as retaining the optical fiber 2 and, in this condition, actuates the laser oscillator 1 to irradiate the affected part with a laser beam through the front-end 1a, a relevant anatomy of the patient can be evaporated in a moment of time to carry out intended medical treatment. It is to be noted that in the laser beam irradiation device shown in the figure, although nothing is attached to the front-end of the optical fiber 1, a handle (not shown) may be attached thereto so that the physical, who is an operator, can use the device easily.

Besides the laser oscillator 2 and the optical fiber 1, the laser beam irradiation device A includes a container 3 that contains a processing agent containing metal powder that can absorb a laser beam. The processing agents are prepared as a fine particle 4 having metal powder as its main component, a liquid 5 obtained by mixing the fine particle 4 into water etc., and an impregnated body 6 impregnated with the fine particle 4 or the liquid 5 so that one of the fine particle 4, the liquid 5, and the impregnated body 6 may be selected and used.

In the present example, as the laser oscillator 2 an Nd:YAG laser is used which emits a laser beam having a wavelength of 1064 nm, as the optical fiber 1 such a fiber is used that, as shown in FIG. 3, its core 11 is made of quartz glass and its clad is made of polymer, and as the metal powder that is the main component of the processing agent and that can absorb a laser beam, titanium oxide ($TiO_2$) is used.

The following will describe a method for machining the front-end 1a of the optical fiber so that it may taper down by using the laser beam irradiation device A having such a configuration as given above. First, the rear end 1b of the optical fiber 1 is connected to the laser oscillator 2 and a coating of the front-end 1a is removed to expose the clad 12 and, in this condition, the front-end 2a is put into the processing agent (for example, the liquid 5).

It is here to be noted that naturally how to put the front-end 1a of the optical fiber 1 into the processing agent differs with the nature of the processing agent. That is, in the case where the processing agent is, for example, the fine particle 4 or the liquid 5 that has some fluidity, the front-end 1a of the optical fiber 1 is inserted into the fine particle 4 or the liquid 5. In the case where the processing agent is the impregnated body 6, the front-end 1a of the optical fiber 1 is inserted into the impregnated body so that it may be soaked into or brought into contact with the impregnated body.

In such a condition where the front-end 1a of the optical fiber 1 is soaked in the liquid 5, the laser oscillator 5 is actuated to emit a laser beam. The laser beam emitted from the laser oscillator 2 is applied into the liquid 5 from the front-end 1a of the optical fiber 1 and absorbed by the metal powder. When having absorbed the laser beam, the metal powder is evaporated or decomposed rapidly, due to an action of which the front-end 1a of the optical fiber 1 is machined. As a result of this machining, the front-end 1a of the optical fiber 1 is tapered as shown in FIG. 1 or any one of FIGS. 2A–2G.

At a tapered portion of the front-end 1a of the optical fiber 1 machined by the machining method related to the present invention, the core 11 is exposed. Therefore, the laser beam is radiated from all the surface of the tapered portion, so that energy of the laser beam is not concentrated to one point but scattered to a wide range. Therefore, it is advantageous when energy is widely distributed to a wide area in operation. As an operation that such an energy distribution is preferable, there are dermatology treatment and dentistry pulp canal treatment.

Therefore, when such an operation is performed that it is necessary to concentrate laser beam energy to extremely small one point, preferably a film is formed on a slant face of the tapered portion so that irradiation from this slant face may be blocked off.

The above-described machining method and laser beam irradiation device for realizing this machining method according to the present invention are advantageous if employed for use in medical treatment.

What is claimed is:

1. A method for machining a front-end of an optical fiber for guiding a laser beam emitted from a laser oscillator to a target, so that the front-end of the optical fiber may taper down, the method comprising the steps of:
    exposing a clad of the optical fiber adjacent the front end of the optical fiber, and attaching an end of the optical fiber opposite the front end to the laser oscillator;
    preparing a processing agent containing metal powder that can absorb the laser beam emitted from the laser oscillator connected to the optical fiber;
    soaking the front end of the optical fiber in the processing agent; and emitting the laser beam from the laser oscillator, so as to machine the front-end of the optical fiber into a tapered form.

2. The method according to claim 1, wherein the processing agent containing the metal powder is a liquid.

3. The method according to claim 1, wherein the metal powder contains at least titanium oxide.

4. The method according to claim 1, wherein the laser beam is a Nd:YAG laser beam, and the metal powder contains at least titanium oxide.

5. An end processing device for optical fiber comprising:
a laser oscillator;
an optical fiber connected at a rear end to the laser oscillator for guiding a laser beam emitted from the laser oscillator in such a manner that a target region may be irradiated with the laser beam from a front end of the optical fiber; and
a retaining member containing a processing agent which contains metal powder that can absorb the laser beam emitted from the laser oscillator, and which is used to machine the front end of the optical fiber into a tapered form.

6. The end processing laser device for optical fiber according to claim 5, wherein the processing agent is a liquid, and the retaining member is a liquid container.

7. The end processing device for optical fiber according to claim 5, wherein the metal powder contains at least titanium oxide.

8. The end processing device for optical fiber according to claim 5, wherein the laser beam is a Nd:YAG laser beam, and the metal powder contains at least titanium oxide.

* * * * *